United States Patent [19]

Prindiville et al.

[11] Patent Number: 5,313,513
[45] Date of Patent: May 17, 1994

[54] ANNULAR COMPUTED TOMOGRAPHY

[75] Inventors: James E. Prindiville, Antioch; Michael P. Skipalis, Vallejo; Hayden G. Martin, Dublin, all of Calif.

[73] Assignee: The United States of America as represented by the Secretary of the Navy, Washington, D.C.

[21] Appl. No.: 59,846

[22] Filed: May 11, 1993

[51] Int. Cl.$^5$ ................ G01N 23/18; G01B 15/06
[52] U.S. Cl. .................. 378/4; 364/413.13; 364/413.14; 364/413.15; 364/552; 378/20; 378/901
[58] Field of Search .............. 378/4, 10, 19, 20, 901; 250/360.1; 364/413.14, 413.15, 413.16, 413.17, 413.21, 508, 571.03

[56] References Cited

U.S. PATENT DOCUMENTS

| | | | |
|---|---|---|---|
| 2,748,290 | 5/1956 | Reichertz | 250/360.1 |
| 3,766,387 | 10/1973 | Heffan et al. | 378/58 |
| 4,422,177 | 12/1983 | Mastronardi et al. | 378/17 |
| 4,725,963 | 2/1988 | Taylor et al. | 364/507 |
| 4,888,693 | 12/1989 | Tam | 364/413.16 |
| 5,027,378 | 6/1991 | Fujii et al. | 378/11 |
| 5,060,250 | 10/1991 | Kwee et al. | 378/61 |
| 5,210,688 | 5/1993 | Cheu et al. | 364/413.19 |

Primary Examiner—Paul M. Dzierzynski
Assistant Examiner—David Vernon Bruce

[57] ABSTRACT

A Computed Tomography system for obtaining annular views of cylindrical objects, in which x-ray scanning is done of an annulus of the objects, and the computation necessary to derive the reconstructed image in polar coordinates is limited to the annulus of the objects, ignoring the other areas. Normalization is done to adjust the reconstructed image to the number of scans made of the various areas of the object.

8 Claims, 3 Drawing Sheets

ANNULAR COMPUTED TOMOGRAPHY

BACKGROUND OF THE INVENTION

This invention relates to the examination of objects using a system of computed tomography (CT). CT is ordinarily used to examine the complete cross section of an object being studied, whether or not the entire object is of interest. When only an annular ring of the object is of interest, it is still necessary to scan the entire object, do the computations necessary for the entire object, and ignore the core of the object as not of interest.

U.S. Pat. No. 4,422,177 to Richard Mastronardi et al (1983) undertakes to do CT scanning of tubular objects such as rocket motors, but data concerning the entire cross-section is provided in a conventional manner to a computer for apparently conventional computations.

U.S. Pat. No. 4,725,963 to Morris Taylor et al (1988) discloses a CT system for inspecting cross-sections of tubes, but the scanning and computation do not allow the system to ignore the core of the tube.

U.S. Pat. No. 4,888,693 to Kwok C. Tam (1989) discloses a CT system for estimating the outer boundary or hull of an object, but the purpose of this system is not to examine the periphery of the object but to determine the position of the discontinuity between inside and outside the object.

SUMMARY OF THE INVENTION

It is the object of the present invention to examine hollow and solid cylindrical objects in cross-section by CT scanning. In the preferred use, the cylindrical objects being examined are the outer portions of rocket motors, but any hollow or solid cylindrical object falls within the intended scope of the invention.

In the preferred embodiment of the invention, we scan with x-rays and detect the attenuation of these x-rays after they have passed through only an annulus, which may be the outer periphery or an interior annulus, of the object of interest. By then conducting the calculations of backprojection of the CT data in a polar co-ordinate system which ignores or normalizes out any data concerning the core of the object in the normalized reconstructed image, calculation time can be greatly shortened over that required for reconstruction of data on the entire cross-section of the object.

Using an equivalent number of projectors and equivalent sampling parameters, an Annular Computed Tomography (ACT) reconstruction process provides a much higher resolution image of an annulus rather than a full CT reconstruction. In ACT the same number of detectors are sampling a smaller radial extent. In ACT the same number of reconstruction grid elements covers a smaller physical area. ACT, as compared with CT, requires a reduced data set for equivalent reconstruction grid sizes. Since there can be fewer data points, data collection time and computational time are significantly reduced. Unlike CT, a ACT image can be reconstructed and displayed well before an entire object is scanned. A particular reconstruction grid element is included in only a small segment of the data set needed for 360° reconstruction. Once that data is collected, a complete reconstruction of that grid element can be achieved.

A given feature in an object is sampled in every angular view of a conventional CT system. In a ACT system, a given feature is only sampled in a small tangential arc. This small tangential arc represents the best x-ray transmission contrast for many features, such as rocket motor case unbonds. Other samples would be taken through the bulk of the object. CT, by averaging the best and worst angular orientations of a feature, reduces the contrast resolution of many features. ACT avoids this problem, by using only data in the small tangential arc.

By displaying ACT reconstructions in a polar coordinate grid $(\rho, \theta)$ or (rho, theta), circumferential features of the object can be aligned with their long axis crossing raster lines of video display units. This provides an increased probability of detection of these circumferential features. Narrow features are not lost in the raster lines.

DESCRIPTION OF THE PREFERRED EMBODIMENT

Figure 1:
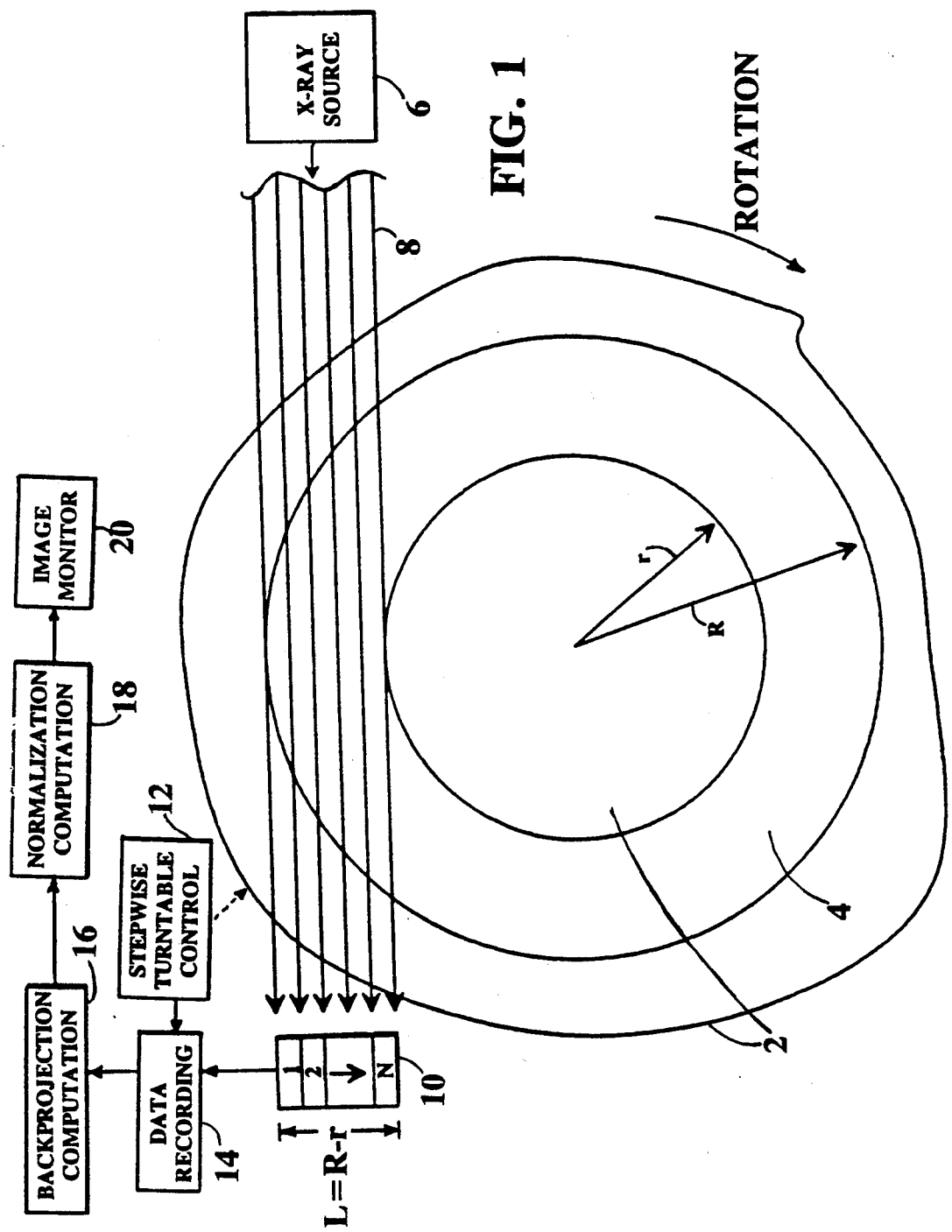
FIG. 1 a cross sectional view of a cylindrical object being scanned by an x-ray source and an accompanying array of detectors.

Referring to FIG. 1, a cylindrical object 2, having an essentially circular cross-section and a reconstruction ring 4 of interest of outer radius R extending inward to a radius r, is to be examined. An x-ray source 6 provides an x-ray beam 8, which passes through the complete width of the reconstruction ring to be detected by an array detector 10 comprising a linear array of detectors (1, 2, . . . N). There is an arrangement to allow stepwise relative rotation between the object 2 and the path of x-ray beams 8. This is conveniently done in most instances by rotating the object in a stepwise fashion on a turntable under the control of a stepwise turntable control 12. The resulting x-ray attenuation data from the detector 10 is recorded at each step in a data recording device 14. Using techniques disclosed below, the backprojection values for the recorded data are computed by backprojection computation 16, and then those values are normalized as disclosed below by normalization computation 18. The resulting normalized backprojection values are displayed on an image monitoring device 20.

Figure 2:
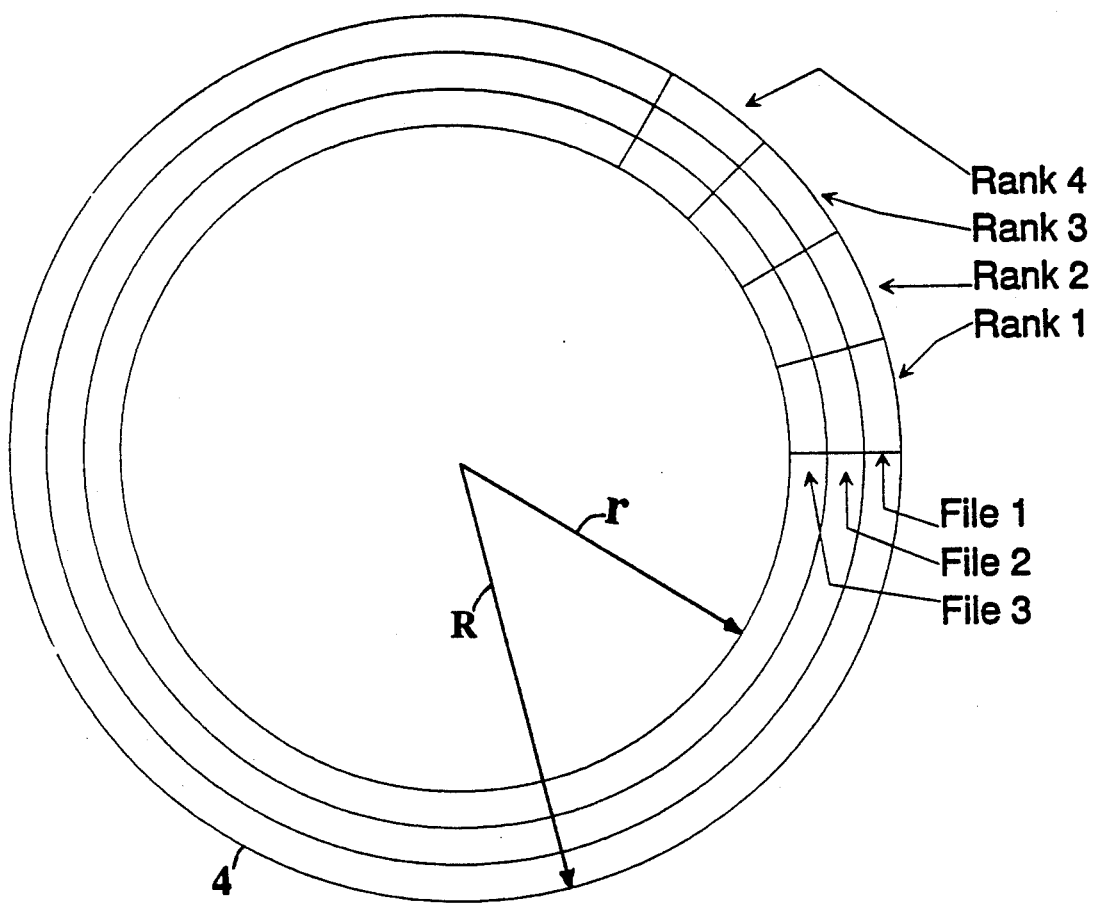
FIG. 2 is a cross sectional view of the cylindrical object, showing the labels applied to the different polar coordinate regions or voxels.

Referring to FIG. 2, the reconstruction ring 4 is divided for scanning and computational purposes into polar coordinate areas called voxels. The outermost annulus in the reconstruction ring is called File 1, and the succeeding annuli proceeding inwardly are called File 2, File 3, and so on, for whatever number of annuli computation is convenient. Each annulus is divided into a group of angular segments, corresponding to the area which is tangential to the x-ray beam during each succeeding step of the stepwise rotation. These angular segments are defined as Rank 1, Rank 2, Rank 3, and so on, for whatever number of angular segments is convenient. A voxel is all that part of any one rank which falls within any one file.

Figure 3:
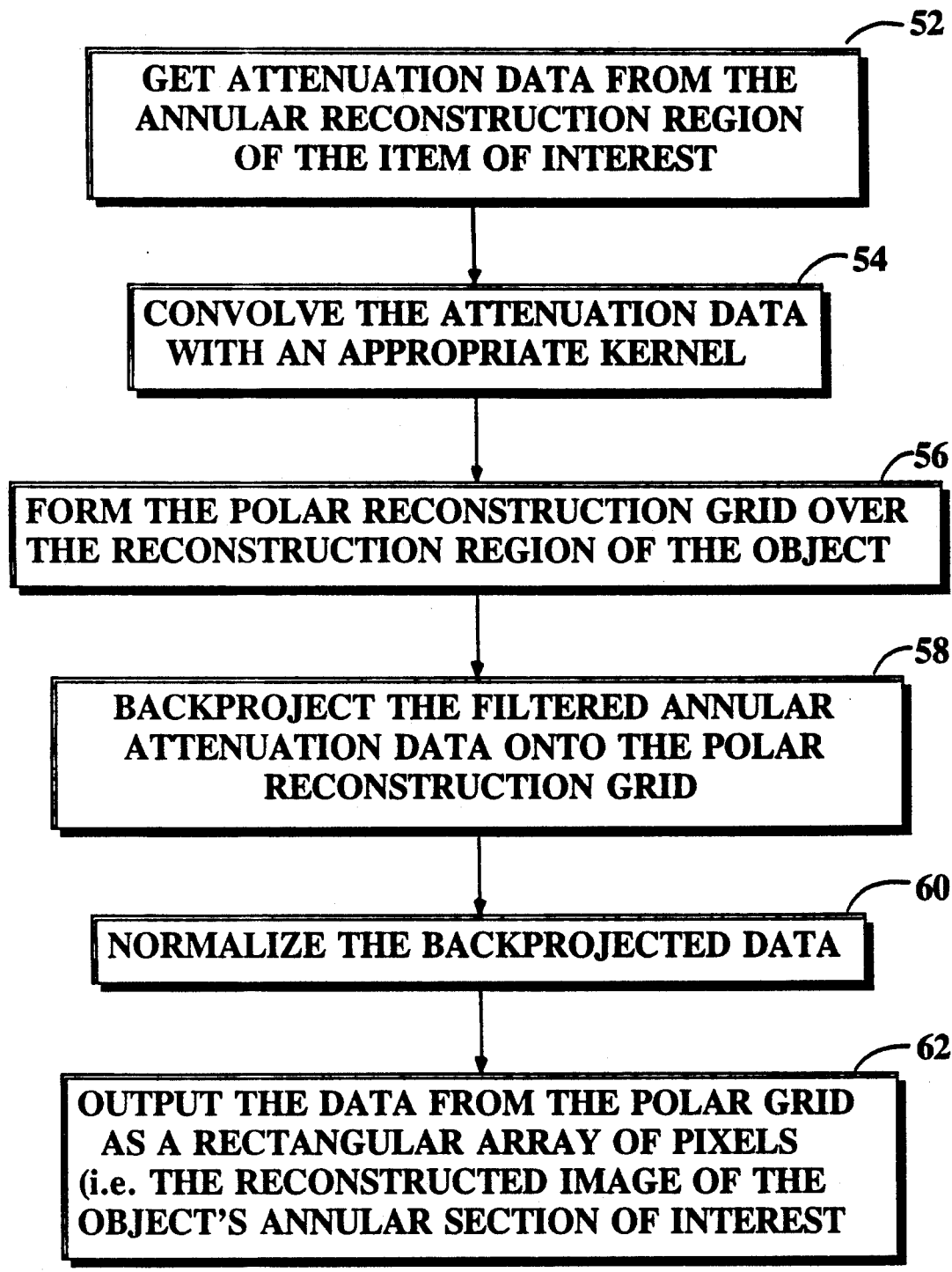
FIG. 3 is a flow chart of the steps in the procedure of conducting the scan and reconstructing the image of an annular section of the object, which we call the reconstruction ring.

FIG. 3 shows a flow chart giving the broad steps involved in carrying out the procedure described herein. Each step is described in more detail hereinafter.

Step 52 is to get attenuation data from the annular reconstruction region of the item of interest. Step 54 operates on this attenuation data and convolves the attenuation data with an appropriate kernel. Step 56 is to form a polar reconstruction grid for computational purposes over the reconstruction region of the object. Step 58 is to backproject the filtered annular attenuation data onto the polar reconstruction grid. Step 60 normalizes the backprojected data. And finally, step 62 outputs the data from the polar grid as a rectangular array of pixels (that is, as the reconstructed image of the reconstruction region of the object).

The explanation has reached the stage where a more detailed presentation of the steps involved is appropriate.

To use the present system, it is first necessary to get the x-ray attenuation data from the reconstruction region of the object being studied. In this process there must be relative movement between the object and the source/detector system. For this discussion it is assumed that the object will be rotated (as on a turntable) and that the source/detector system will remain fixed, but the opposite is also a possibility.

Place the object on a turntable which can be rotated in precise increments. The location of the center of rotation of the turntable must be known. The same thing might be done with a standard Computed Tomography (CT) scan, and the same caveats about precision of location, bearing, runout, etc., apply. The outer radius of the reconstruction ring is given the label R.

A detector package 10 is placed on a level with the circular cross section of the object. The detectors can be anything which can measure the intensity of an x-ray beam transmitted through the object. The detector package will be placed on the opposite side of the object from the x-ray source 6. The outermost detector will be placed so that it will detect x-rays from the source which pass through the outer edge of the reconstruction ring 4. The innermost detector measures the attenuation of x-rays passing through the object at a minimum radius which is given the label r. The width of the reconstruction ring which is covered by the system is $R-r$. For parallel x-ray beams, this is equal to L, the length of the detector package. For divergent (fan) x-ray beams, the width of the reconstruction ring $(R-r)$ will be less than L. In the present system, the width of the reconstruction ring is much smaller than the inner radius of the reconstruction ring, i.e., $R-r << r$. The detectors are equally spaced, starting at the outer portion of the reconstruction ring and going inward. The number of detectors is given the label N. The width of a detector is given the label W, whereby $L=NW$.

An x-ray source is placed on a level with the detectors and centered on them. The source is placed on the opposite side of the object from the detectors, so the radiation will pass through the reconstruction ring of the object to the N equally spaced detectors.

A decision must be made on the number of views which are to be taken of the object. The number of views is given the label M. If M is too small, only gross structures in the object will be resolved in the reconstructed image. As M becomes larger, the computational burden increases. If M becomes too large, the computational burden increases with no corresponding improvement in the final reconstructed image. The choice of M must depend upon what is to be viewed, the necessary level of resolution, and the allowed time for computation. No general choice can be given.

Give the amount of angular rotation of the object from one view to the next the label t. Give the angular extent of the reconstruction ring to be imaged the label A. If the entire ring is to be viewed, then $A=2\pi$ radians. It follows that $t=A/M$. The section of the reconstruction ring from zero radians to A radians will hereinafter be referred to as the reconstruction region.

A series of detector readings D will be obtained for angular rotation view i, where i ranges from 1 (the first) to M (the last), and for detector j, where j ranges from 1 (the outermost) to N (the innermost). The detector readings will be generally labeled $D_{i,j}$. The recorded detector readings must be in the attenuation line integral form, not in the transmittance form.

When the detector readings have been obtained, they are convolved with an appropriate kernel, in the same manner as is done in standard CT. There is nothing new in the way it is done in the present invention.

The next step is to form the polar reconstruction grid over the reconstruction region of the object. Annular Computed Tomography (ACT) voxels are sections of annuli of the object being scanned. The outermost annulus includes the outer boundary of the reconstruction ring and extends inward a distance which is called gr. The next annulus is inside the first annulus and contiguous with it. It also extends a distance gr. Continue defining annuli in the same manner until the entire reconstruction ring is contained in the annuli. Next, starting at zero degrees, define contiguous sectors of angular size gc_ang. The value of gc_ang is adjusted so that an integral number of contiguous sectors divide the object. These sectors divide the annuli into our ACT voxels. If gr or gc_ang is too big, only gross structures in the object will be resolved in the final reconstructed image. As gr and gc_ang grow smaller, the computational burden increases, eventually with no corresponding improvement in the reconstructed image.

Next it is necessary to adjust the variables "ranks" and "files". The variable "files" is the number of annuli in the polar reconstruction grid; "files" must be an integer. Since we do not wish to waste voxels on locations where no data was taken, we adjust gr so that the "files" annuli exactly covers the width of the reconstruction ring. The width of the reconstruction ring is $(R-r)$, and when it is divided by gr a result is obtained which may not be an integer. The ceiling function is then used to force an integer result. This can be written as "Let files:=ceiling{$(R-r)$/gr}". The value of "files" is then used to adjust gr; and this can be written as "Let gr:=$(R-r)$/files." The ceiling is used rather than the floor so that if gr is changed by this procedure, it is not made worse than the value selected by the user.

The variable "ranks" is the number of sectors in the polar reconstruction grid; "ranks" must be an integer. If A (the angular extent to be viewed) is $2\pi$ radians, then we must adjust gc_ang to insure that there is no overlap of the voxels. However, even if $A < 2*\pi$ radians, we would not wish to waste voxels on locations which will not be imaged, so we adjust gc_ang in any case. It is adjusted so that "ranks" sectors exactly covers the angular extent to be viewed. Divide A by gc_ang, and apply the ceiling function (to guarantee an integer result). This can be written as "Let ranks:=ceiling {A/gc_ang}". The value of "ranks" is then used to adjust gc_ang. This can be written as "Let gc_ang:=A/ranks". The ceiling is used rather than the floor so that if gc_ang is changed by this procedure, it is not made worse than the value selected by the user.

Calculations are only carried out for the center of each voxel, called a grid point, and the voxels are assumed to be small enough that a value at the center will be approximately correct throughout the entire voxel. The polar reconstruction grid is represented by the "ranks" by "files" array of voxel center points. Each point is defined by a radius and an angle. The first grid point g_pt$_{1,1}$ has a radius g$\rho_1$ which is 0.5 gr less than the radius of the object, which can be written "Let g_rho1:=R−0.5*gr" and an angle g$\theta_1$ of 0.5 gc, which can be written "Let g_theta1:=0.5*gc".

The calculations for voxel center points are made and recorded while stepping through the "files" values of g_rhoj or g$\rho_j$ from j=1 to j=files while nested in another stepping sequence through the "ranks" values of g_thetai or g$\theta_i$ from i=1 to i=ranks to obtain values for each of the grid points g_pt(i,j) for each of the ranks and files.

It is next necessary to convolve, or filter, the attenuation data with an appropriate kernel. This is not part of the present invention. It is done in standard Computed Tomography. It is not necessary to describe it further in this application.

The next step is to backproject the filtered annular attenuation data onto the polar reconstruction grid. With only one exception, annular CT backprojection is identical to standard CT backprojection. In standard CT backprojection, one finds the intersection of the detector plane with the line defined by a point on the radiation source and a grid point g_pt$_{j,k}$. If this intersection point lies within the detector package, one uses interpolation to calculate the attenuation line integral as if a detector had been at the intersection point. This interpolated attenuation datum is added to the accumulating attenuation for that grid point. In annular CT there may be no data for a particular grid point in a particular view because the intersection point may fall outside of the detector package. Compensation must be done for this, and we do so in the normalization portion of the flow diagram.

In the backprojection, there is a loop from k=1 to k="files" nested in a loop from j=1 to j="ranks" nested within a loop from i=1 to i=M. At the center of the inner loop is a function to backproject the data in view i onto grid point g_pt(j,k).

The next step is to normalize the resulting data. In this step there is a loop running from k=1 to k="files" nested within a loop running from j=1 to j="ranks". Inside the inner loop is a function to count the number of data points backprojected into g_pt(j,k). If the count is zero, no data has been derived for that grid point, and the data value is set to some value that is unlikely to occur in the final image, such as zero or 255, depending upon which makes the final reconstructed image easier to read. If the count is other than zero, divide the interim data value for grid point g_pt(j,k) by the count for that point to obtain a normalized value for that grid point to compensate for the unequal number of backprojection values for different grid points in Annular Computed Tomography.

Instead of displaying the circular form of the annulus that is reconstructed, data may be mapped to a rectangular grid with one axis representing rho (distance from the center of the reconstruction grid element) and the other axis representing theta (the angular position of the reconstruction grid element). Thus a narrow annular reconstruction can be displayed as a long narrow rectangle, straightening the annulus, but making an insignificant difference in the display of any small segment. This mapping gives greater emphasis to circumferential features, which are normally of the greatest interest to inspections of this nature. As grid elements are measured to complete the arc required for reconstruction, they can be immediately displayed, before all data points have been collected. The reconstructed data can be displayed on the image monitor and can be moved across the monitor for human inspection as sufficient data is obtained for each portion.

There are possible alternatives to the system described above. The ACT reconstruction grid is in a polar coordinate annulus. This makes the voxel size of the elements vary with radial change. Changing the grid so that the element size is constant may improve resolution of features furthest from the center of the grid. Reconstructions can be made from two dimensional data sets, such as film x-rays or radioscopic images. By taking into account the conical nature of the x-ray beam, these images can be used to make a stack of reconstructions covering a large vertical distance.

We claim:

1. A method of conducting computed tomography examination of an annulus of interest in an object, said annulus having a radial thickness which is substantially shorter than its radius, while ignoring the core of the object, the radius of the annulus defining, in rotation, a plane, comprising the steps of
   a. passing a group of x-ray beams in said plane through the object,
   b. detecting the attenuation of said x-ray beams at an array of points in said plane after the x-ray beams have passed through the annulus of interest, the array of points extending across the path of the x-ray beams for a distance substantially shorter than said radius,
   c. causing stepwise relative rotational motion between the x-ray beams and the object,
   d. recording data defining said attenuation for each of the points in said array of points for each step of said stepwise rotational motion,
   e. backprojecting the recorded attenuation data onto an array defining a recorded interim reconstructed image, and
   f. normalizing the array defining the interim reconstructed image to compensate for the varying number of items of recorded attenuation data used in constructing the interim image by backprojection, thereby to generate the final reconstructed image.

2. A method according to claim 1 wherein the x-ray beams pass along a fixed path, and the step of causing stepwise relative rotational motion between the x-ray beams and the object is caused by rotating the object in steps of equal angular size.

3. A method according to claim 2, further comprising the use of an array of equally spaced detectors to detect the attenuation of the x-ray beams at said array of points.

4. A method according to claim 1, wherein the step of normalizing the array is carried out by counting the number of times recorded information is used by backprojection in deriving the data in each grid point in the reconstructed image, and dividing the interim value of the reconstructed image in each grid point by said number of times to derive a value in the final reconstructed image, and further, for grid points where said number of times is zero, assigning those grid points a value in the final reconstructed image which is uniformly of a particular value unlikely to otherwise occur in the final image.

5. A system for conducting computed tomography examination of an annulus of interest in an object, said annulus having a radial thickness which is substantially shorter than its radius, while ignoring the core of the object, the radius of the annulus defining, in rotation, a plane, comprising the steps of
   a. an x-ray source directing a group of x-ray beams in said plane through the object,
   b. an array detector situated to detect the attenuation of said x-ray beams at an array of points in said plane after the x-ray beams have passed through the annulus of interest, the array of points covered by the array detector extending across the path of the x-ray beams for a distance substantially shorter than said radius,
   c. a stepwise rotator producing stepwise relative rotational motion between the x-ray beams and the object,
   d. a data recorder for storing the data defining said attenuation for each of the points in said array of points for each step of said stepwise rotational motion,
   e. computer means for backprojecting the recorded attenuation data onto an array defining a recorded interim reconstructed image, and
   f. additional computer means for normalizing the array defining the interim reconstructed image to compensate for the varying number of items of recorded attenuation data used in constructing the interim image by backprojection, thereby to generate the final reconstructed image, and
   g. monitor means for viewing the final reconstructed image.

6. A system according to claim 5 wherein the X-ray beams pass along a fixed path, and the stepwise rotator rotates the object in steps of equal angular size.

7. A system according to claim 6, wherein the array detector comprises an array of equally spaced detectors to detect the attenuation of the x-ray beams at said array of points.

8. A system according to claim 5, wherein the additional computer means for normalizing the array comprises means for counting the number of times recorded information is used by backprojection in deriving the data in each grid point in the reconstructed image, and means for dividing the interim value of the reconstructed image in each grid point by said number of times to derive a value in the final reconstructed image, and the additional computer means further comprising, for grid points where said number of times is zero, means for assigning those grid points a value in the final reconstructed image which is uniformly of a particular value unlikely to otherwise occur in the final image.

* * * * *